(12) United States Patent
Brimhall (10) Patent No.: US 7,798,994 B2
(45) Date of Patent: Sep. 21, 2010

(54) NEEDLE SHIELD TO SEPTUM INTERCONNECT

(75) Inventor: Greg L. Brimhall, West Jordan, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 523 days.

(21) Appl. No.: 11/274,230

(22) Filed: Nov. 15, 2005

(65) Prior Publication Data

US 2007/0112305 A1 May 17, 2007

(51) Int. Cl.
*A61M 5/00* (2006.01)
(52) U.S. Cl. ..................................... 604/110
(58) Field of Classification Search ............... 604/110, 604/198, 200–206, 263
See application file for complete search history.

(56) References Cited

U.S. PATENT DOCUMENTS

| | | | |
|---|---|---|---|
| 4,998,925 A * | 3/1991 | Al-Sioufi et al. ............ 604/533 |
| 5,135,504 A | 8/1992 | McLees |
| 5,215,525 A | 6/1993 | Sturman |
| 5,215,528 A | 6/1993 | Purdy et al. |
| 5,312,359 A | 5/1994 | Wallace |
| 5,328,482 A | 7/1994 | Sircom et al. |
| 5,447,501 A | 9/1995 | Karlsson et al. |
| 5,458,658 A | 10/1995 | Sircom |
| 5,562,631 A | 10/1996 | Bogert |
| 5,562,633 A | 10/1996 | Wozencroft |
| 5,573,510 A | 11/1996 | Isaacson |
| 5,584,809 A | 12/1996 | Gaba |
| 5,599,310 A * | 2/1997 | Bogert ................... 604/164.12 |
| 5,601,536 A | 2/1997 | Crawford et al. |
| 5,651,772 A | 7/1997 | Arnett et al. |
| 5,690,619 A | 11/1997 | Erskine |
| 5,697,907 A | 12/1997 | Gaba |
| 5,700,250 A | 12/1997 | Erskine |
| 5,704,919 A | 1/1998 | Kraus et al. |
| 5,718,688 A | 2/1998 | Wozencroft |
| 5,720,727 A * | 2/1998 | Alexander et al. .......... 604/110 |
| 5,749,856 A | 5/1998 | Zadini et al. |
| 5,810,780 A | 9/1998 | Brimhall et al. |
| 5,810,792 A * | 9/1998 | Fangrow et al. ............. 604/533 |
| 5,853,393 A | 12/1998 | Bogert |
| 5,935,109 A | 8/1999 | Donnan |
| 5,935,110 A | 8/1999 | Brimhall |
| 6,056,726 A | 5/2000 | Isaacson |

(Continued)

FOREIGN PATENT DOCUMENTS

EP 06255753 5/2007

(Continued)

*Primary Examiner*—Kevin C Sirmons
*Assistant Examiner*—Bradley J Osinski
(74) *Attorney, Agent, or Firm*—Mony R. Ghose; Craig Metcalf; Kirton & McConkie (57) ABSTRACT

The present invention is a catheter device. The catheter device will include a septum that is housed within a housing. The septum is designed such that it will seal the housing. The catheter device also includes a needle shield. The needle shield is configured to retain a needle if the needle is withdrawn from the housing. The catheter device is further configured such that the septum includes a receiving portion that is designed to engage a portion of the needle shield. However, if the needle is withdrawn from the housing, the needle shield will disengage from the septum so that the needle shield may be separated from the septum.

14 Claims, 11 Drawing Sheets

U.S. PATENT DOCUMENTS

| | | | |
|---|---|---|---|
| 6,077,244 | A | 6/2000 | Botich et al. |
| 6,206,851 | B1 | 3/2001 | Prosi |
| 6,221,047 | B1 | 4/2001 | Greene et al. |
| 6,224,569 | B1 | 5/2001 | Brimhall |
| 6,287,278 | B1 | 9/2001 | Woehr et al. |
| 6,379,332 | B1 | 4/2002 | Van Landuyt |
| 6,461,362 | B1 | 10/2002 | Halseth et al. |
| 6,506,181 | B2 * | 1/2003 | Meng et al. ............ 604/164.07 |
| 6,595,954 | B1 | 7/2003 | Luther et al. |
| 6,616,630 | B1 | 9/2003 | Woehr et al. |
| 6,652,486 | B2 | 11/2003 | Bialecki et al. |
| 6,663,592 | B2 | 12/2003 | Rhad et al. |
| 6,689,102 | B2 | 2/2004 | Greene |
| 6,695,814 | B2 | 2/2004 | Greene et al. |
| 6,709,419 | B2 | 3/2004 | Woehr |
| 6,719,726 | B2 | 4/2004 | Meng et al. |
| 6,749,588 | B1 | 6/2004 | Howell et al. |
| 2003/0083620 | A1 | 5/2003 | Luther et al. |
| 2004/0078003 | A1 | 4/2004 | Smith et al. |
| 2004/0092889 | A1 | 5/2004 | Ferguson et al. |
| 2004/0193112 | A1 | 9/2004 | Glazier et al. |
| 2004/0225260 | A1 * | 11/2004 | Villa et al. ............. 604/164.01 |
| 2004/0243060 | A1 | 12/2004 | Rossi et al. |
| 2004/0243061 | A1 | 12/2004 | McGurk |

FOREIGN PATENT DOCUMENTS

| | | |
|---|---|---|
| FR | 2846244 | 4/2004 |
| GB | 2343118 A | 5/2000 |

* cited by examiner

NEEDLE SHIELD TO SEPTUM INTERCONNECT

BACKGROUND OF THE INVENTION

The present invention relates to catheter and introducer needle assemblies. In medicine, such catheter and introducer needle assemblies are used to place a catheter properly into the vascular system of a patient. Once in place, catheters such as intravenous (or "IV") catheters may be used to infuse fluids including normal saline, medicinal compounds, and/or nutritional compositions (including total parenteral nutrition, or "TPN") into a patient in need of such treatment. Catheters additionally enable the removal of fluids from the circulatory system and monitoring of conditions within the vascular system of the patient.

One type of commonly-used catheter is a peripheral intravenous catheter. These short, indwelling intravenous catheters are often used to provide an entry route for medications, fluid for hydration, and in some cases, for parenteral feeding, into a patient. Such catheters are generally short in length, ranging from about one-half to about three inches in length, and are generally made of flexible biocompatible materials. In some cases, these catheters additionally include a radiopaque compound such as barium sulfate to allow the location of the catheters to be tracked once inside the body.

Peripheral IV catheters are often provided as "over-the-needle" catheters mounted over an introducer needle with a sharp distal tip. This sharp tip often includes a bevel intended to be oriented away from the patient's skin during penetration of the skin. A portion of the catheter including at least the distal tip of the catheter securely grips the outside of the needle to prevent catheter peelback during insertion of the catheter into the circulatory system of the patient. Although several techniques for placing such catheters are practiced in the art, many generally include the step of inserting at least a portion of the needle into the target vessel and then sliding the catheter over the needle into place.

The medical worker then attempts to verify proper placement of the catheter within the blood vessel. Catheter and introducer needle assemblies have been provided that include means for verifying proper placement of the catheter in a blood vessel. One such means is a "flashback chamber" that is viewable to the clinician during installation. This chamber receives a small quantity of blood when a vessel is entered, thus allowing observation of blood in the chamber to be an indicator of successful entry into a vessel. Flashback notification may also be provided by providing a notch in the introducer needle a distance from the sharp distal tip of the needle in a region that is housed within the catheter. Blood flashback may then be observed at the notch and regions near it within the catheter when the catheter is at least somewhat transparent.

Once placement of the needle has been confirmed, the user may temporarily occlude flow to the blood vessel, remove the needle, leaving the catheter in place, and attach a device to the catheter for fluid removal, input, or to seal the catheter. This process has been somewhat difficult in practice since many placement sites simply do not allow easy occlusion of the target vessel. Additionally, even when such occlusion is achieved, it may be imperfect, thus resulting in blood leaking from the catheter, endangering the medical personnel employing it.

"Needle shields" or needle-shielding devices have also been used with catheters. These devices are designed such that when the needle is withdrawn from the patient, the needle tip will be trapped/captured within the needle shield. The purpose of these needle shield devices is to house the tip of the needle in a secure location so that the needle tip will not accidentally be injected/impaled into the nurse, the doctor, etc.

Catheter and introducer needle assemblies have thus been provided in the art that provide a variety of seals or "septa" for preventing outflow of fluid during and following removal of the introducer needle. These structures are generally elastomeric plates designed to closely conform to the shape of a needle during storage and use to prevent leaking, then to seal upon removal of the needle. These septa need to be elongated in needles with flashback notches so as to encapsulate the notch and needle tip during needle removal in order to prevent the unwanted escape of blood. This elongation of the septa increases the amount of friction placed on the needle, the amount of effort needed to remove it, and the potential of damaging the product. In order to overcome this, septa have been developed that include an internal cavity that has an internal diameter slightly larger than that of the needle used. This results in the needle contacting the septum only in regions outside of this cavity, reducing the surface area in contact with the septum.

However, there is a need in the art for a new type of septa that will engage/interconnect with the needle shield to ensure that the needle will not prematurely separate from the catheter device. Such a device is disclosed herein in the present embodiments.

BRIEF SUMMARY OF THE INVENTION

The present invention is a catheter device that is designed to overcome some of the limitations known in the art. The catheter device may include a needle having a sharp or relatively sharp tip. The needle is designed such that it may be passed through the catheter device. The catheter device also includes a septum that fits within a housing. The septum is made of an elastomeric or other similar material and is designed to seal the housing.

The catheter device will also include a needle shield. The needle shield shown comprises a protective sleeve that is designed to capture/retain the needle tip after it has been withdrawn from the patient. The needle shield is designed to engage the septum. Such engagement may be accomplished by having the septum comprise a receiving portion. Generally, the receiving portion will contact the needle shield and, via friction, hold the needle shield in the proper position.

In some embodiments, the receiving portion comprises an opening into which a front edge of the needle shield may be inserted. Detents and/or nooks designed to augment the engagement between the needle shield and the receiving portion may also be added. In other embodiments, the receiving portion will be a section or portion of a septum housing that extends inward towards the septum and is designed to engage/contact with a portion of a needle shield. Still further embodiments may be designed in which the receiving portion is an interlock feature that is added to the septum. Even further embodiments may have the receiving portion comprise a surface of the septum.

The needle shield is further designed such that if the needle is withdrawn from the housing, the needle shield will disengage from the septum. More particularly, if the needle is withdrawn from the housing, the needle shield will separate from the septum such that the needle shield and the needle may be disposed of properly.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE INVENTION

The presently preferred embodiments of the present invention will be best understood by reference to the drawings, wherein like parts are designated by like numerals throughout. It will be readily understood that the components of the present invention, as generally described and illustrated in the figures herein, could be arranged and designed in a wide variety of different configurations. Thus, the following more detailed description of the embodiments of the catheter device of the present invention, as represented in FIGS. 1A through 7D, is not intended to limit the scope of the invention, as claimed, but is merely representative of presently preferred embodiments of the invention.

Figure 1A:
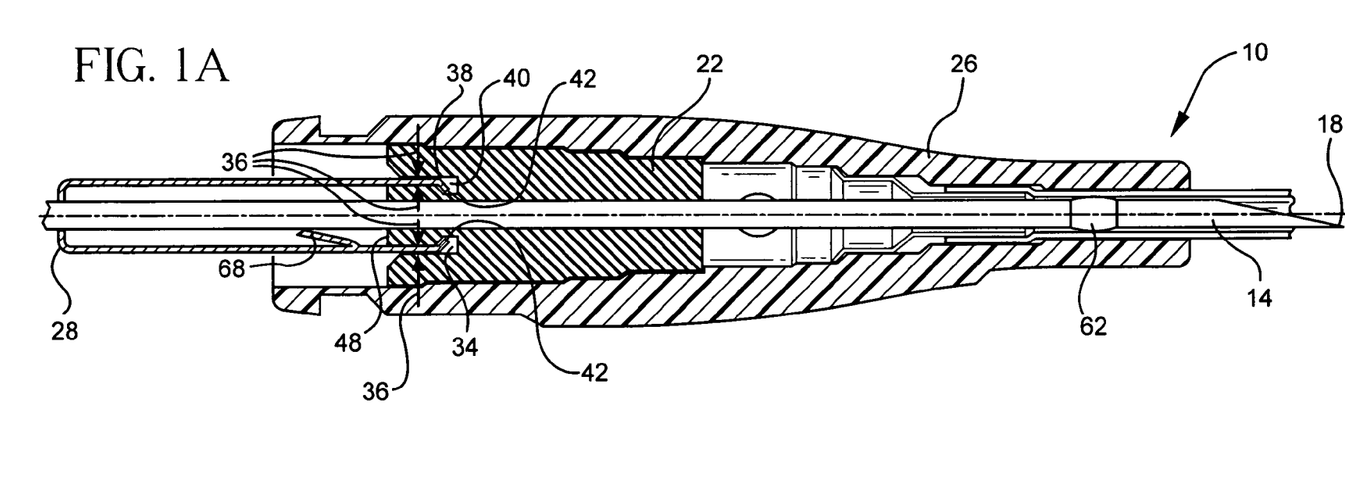
FIG. 1A is a perspective view of a catheter device according to the present invention in which the needle has been passed through the septum.

Referring now to FIG. 1A, a perspective view of a catheter device 10 according to the present embodiments are illustrated. The catheter device 10 may include a needle 14 having a sharp or relatively sharp tip 18. As is known by those of skill in the art, the needle 14 and the needle tip 18 are designed such that the needle 14 may be injected into a patient's vein as a means of introducing into the patient a catheter, an IV, etc.

The catheter device 10 also includes a septum 22 that fits within a housing 26. As is known in the art, the septum 22 is made of an elastomeric or other similar material and is designed to seal the housing 26. Accordingly, if some of the patient's blood begins to leak out during the injection process, the septum 22 will seal/plug the catheter device 10 and prevent blood from flowing past the septum 22.

As shown in FIG. 1A, the housing 26 is designed to engage and retain the septum 22. In some embodiments, this housing 26 is the catheter housing—i.e., the outer wall of the catheter device 10. Of course, other embodiments may be constructed in which the housing 26 is a septum housing—i.e., a wall or enclosure specifically designed to retain the septum 22. Other embodiments may also be made in which the housing 26 is another type of housing.

The catheter device 10 will also include a needle shield 28. As is known in the art, a "needle shield" is a device that is specifically designed such that it will house/retain the needle tip 18 after it has been injected into the patient. More particularly, after the needle tip 18 has been injected into the patient, the needle 14 will be withdrawn so that the IV or catheter may be placed in the patient's vein. Because the needle 14 has been injected into the patient, the needle 14 may be contaminated with the blood-born pathogens present in the patient (which may be, for example, the HIV virus, hepatitis, etc.). Accordingly, once the needle tip 18 is withdrawn from the housing 26, the needle tip 18 will be retained/captured within the needle shield 28, thereby preventing the contaminated needle from accidentally injecting/impaling the clinician, etc.

The needle shield 28 shown in FIG. 1A comprises a protective sleeve that it is designed to capture the needle tip 18 after it has been withdrawn from the patient. (Such capturing will be described in greater detail in conjunction with FIG. 1B). However, such a depiction should not be interpreted as being limiting. Those of skill in the art will recognize that any type of device that is capable of retaining/capturing a needle tip 18 may be used as the needle shield 28.

As shown in FIG. 1A, the needle shield 28 is designed to engage the septum 22. Such engagement may be accomplished by having the septum 22 comprise a receiving portion 34. As used herein, a "receiving portion" 34 is a portion or section of the septum 22 that is configured to receive/engage a portion of the needle shield 28. Generally, the receiving portion 34 will contact the needle shield 28 and, via friction, hold the needle shield 28 in the proper position.

In the embodiment shown in FIG. 1A, the receiving portion 34 comprises an opening into which a front edge 38 of the needle shield 28 may be inserted. Once inserted, friction will hold the needle shield 28 in the proper position (as shown by the force-indicating arrows 36). For further engagement between the needle shield 28 and the receiving portion 34, one or more detents 42 may be added to the front edge 38. Likewise, one or more nooks 40 that are sized and configured to receive the detents 42, may also be added to the receiving portion 34. (Such detents 42 and nooks 40 are shown more clearly in FIGS. 1B and 1C.) Of course, other ways and mechanisms for having the needle shield 28 engage the receiving portion 34 may also be used.

In the embodiment shown in FIG. 1A, there are two receiving portions 34 which have been added to the septum 22. These two receiving portions 34 are separated by a nose 48. In general, the nose 48 will be located proximate to the middle of the septum 22 such that when the needle 14 is passed through the septum 22, the needle 14 passes through all or a portion of the nose 48.

As is shown in FIG. 1A, when the needle 14 is passed through the septum 22 and the nose 48, the needle 14 will cause the septum 22 to expand. In turn, this expansion of the septum 22 reduces the size of the receiving portions 34/openings 34a such that the engagement between the receiving portions 34/openings 34a and the needle shield 28 is much tighter and/or stronger. It is this tight engagement between the needle shield 28 and the receiving portions 34/openings that secures the needle shield 28 in position.

Figure 1B:
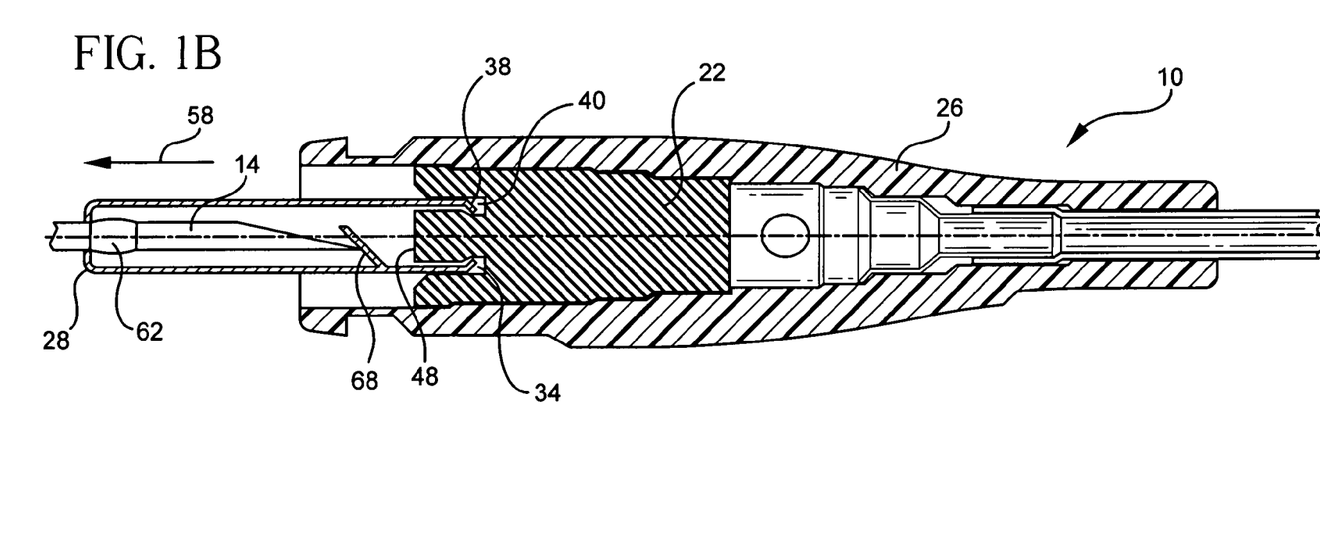
FIG. 1B is a perspective view of a catheter device of FIG. 1A in which the needle has been withdrawn from the septum.

Referring now to FIG. 1B, a perspective view of the catheter device 10 of FIG. 1A is illustrated. However, unlike the situation shown in FIG. 1A, FIG. 1B shows the catheter device 10 after the needle 14 has been withdrawn from the septum 22 and the housing 26 (as illustrated by the movement arrows 58).

As noted above, when the needle 14 is withdrawn from the housing 26, the needle tip 18 will be captured/retained within the needle shield 18. As is known in the art, this capture may be accomplished through the use of a retaining member 60 which is designed to prevent the needle tip 18 from being reinserted into the septum 22. Likewise, a thicker portion 62 on the needle 14 contacts the wall of the needle shield 28 and prevents the needle tip 18 from being pulled out of the needle shield 28.

As shown in FIG. 1B, once the needle tip 18 has been withdrawn from the nose 48, the septum 22 will contract due to the fact that the needle 14 is no longer pushing outwardly against the septum 22. In turn, this contraction of the septum 22 means that the size of the openings increases and the septum nose 48 will no longer contact a portion of the needle shield 28. Retaining member 68 is also illustrated in FIG. 1B.

Figure 1C:
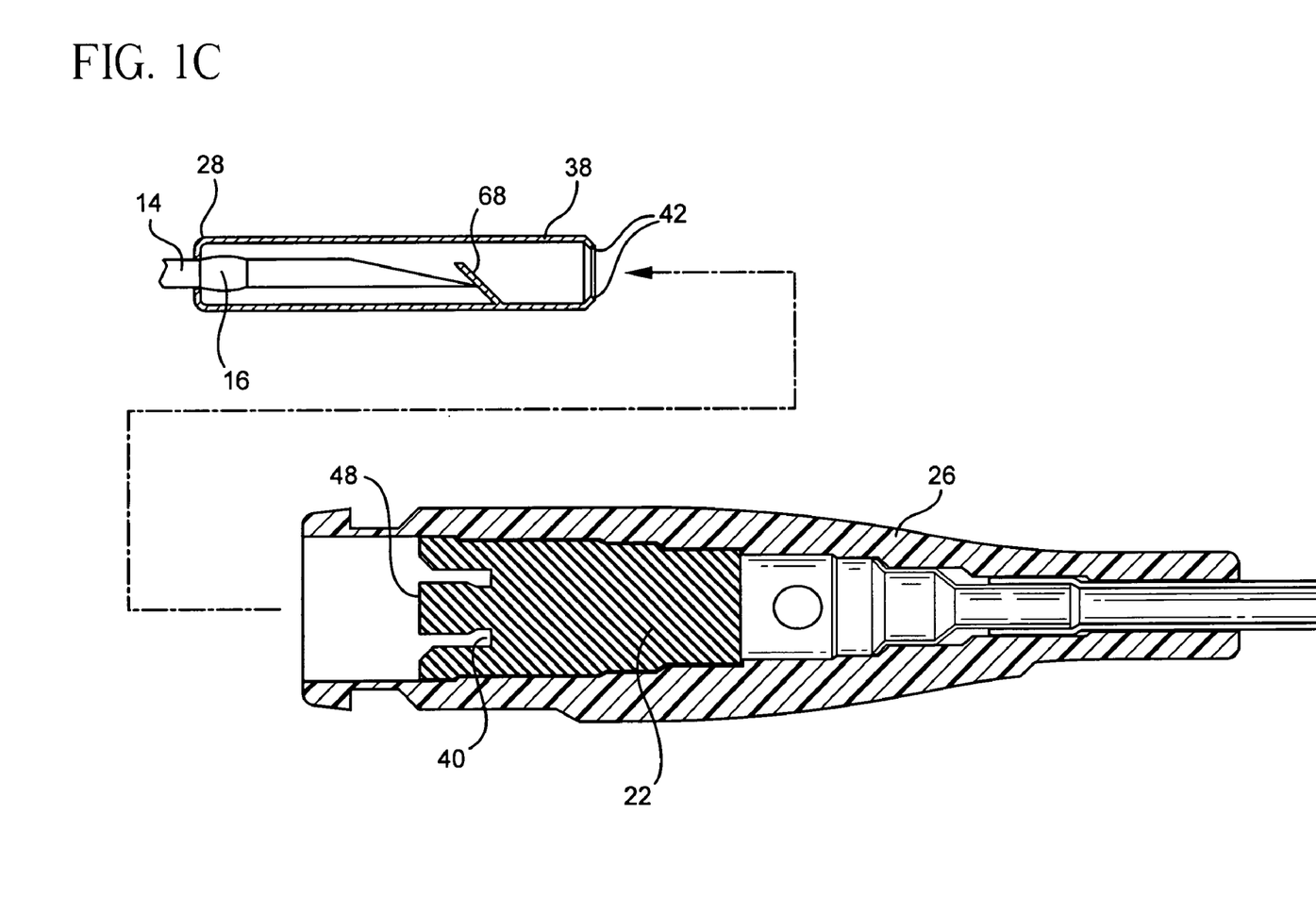
FIG. 1C is a perspective view of a catheter device of FIG. 1A in which the needle shield has been separated from the septum.

Referring now to FIG. 1C, the catheter device 10 of the present embodiments is shown in which the needle shield 28 has been separated from the septum 22. Specifically, as explained above in FIG. 1B, as the needle tip 18 is withdrawn, the septum 22 (and more particularly the receiving portion 34) will no longer engage the needle shield 28. Accordingly, if the user continues to pull the needle 14 in the direction of the arrows 58, the needle shield 28 will separate from the septum 22. Once the needle 14 has been withdrawn and the needle shield 28 separated, the housing 26 and the septum 22 may then be as part of the IV system, the catheter system, etc. FIG. 1C also illustrated feature 16 which is similar in structure to thick portion 62.

Figure 2:
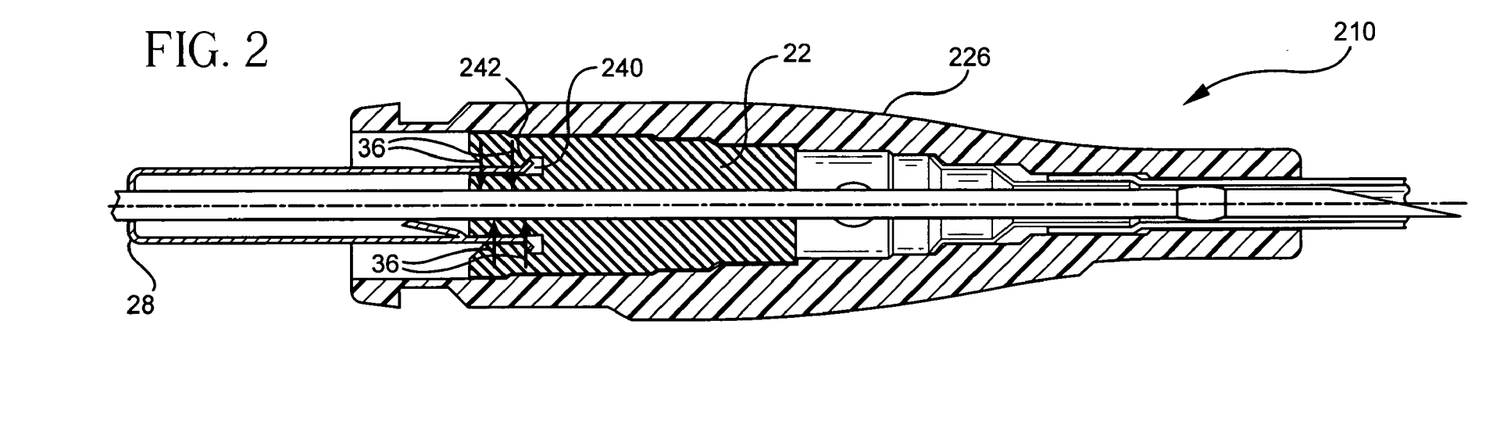
FIG. 2 is a perspective view of another embodiment of a catheter device of the present invention in which the needle has been passed through the septum.

Referring now to FIG. 2, a second embodiment of a catheter device 210 is illustrated. The catheter device 210 is similar to the catheter device 10 shown above in FIGS. 1A-1C. Accordingly, for the purposes of brevity, the above-recited description will not be repeated.

Those of skill in the art will recognize that the difference between the catheter device 10 shown in FIGS. 1A-1C and the catheter device 210 shown in FIG. 2 is the shape/configuration of the detents and the nooks. Specifically, in the catheter 10 shown in FIGS. 1A-1C, the detents 42 and the nooks 40 both point inward—i.e., towards the center of the septum 22. However, in the catheter 210 shown in FIG. 2, the detents 242 and the nooks 240 point outward—i.e., towards the housing 226. In some embodiments, this change in the position/shape of the detents 242/nooks 240 may be desirable in that it may provide greater interaction or engagement between the septum 22 and the needle shield 28. Of course, those of skill in the art will recognize that other shapes, orientations, or configurations of the detents 240 and/or the nooks 240 may also be used.

Figure 3:
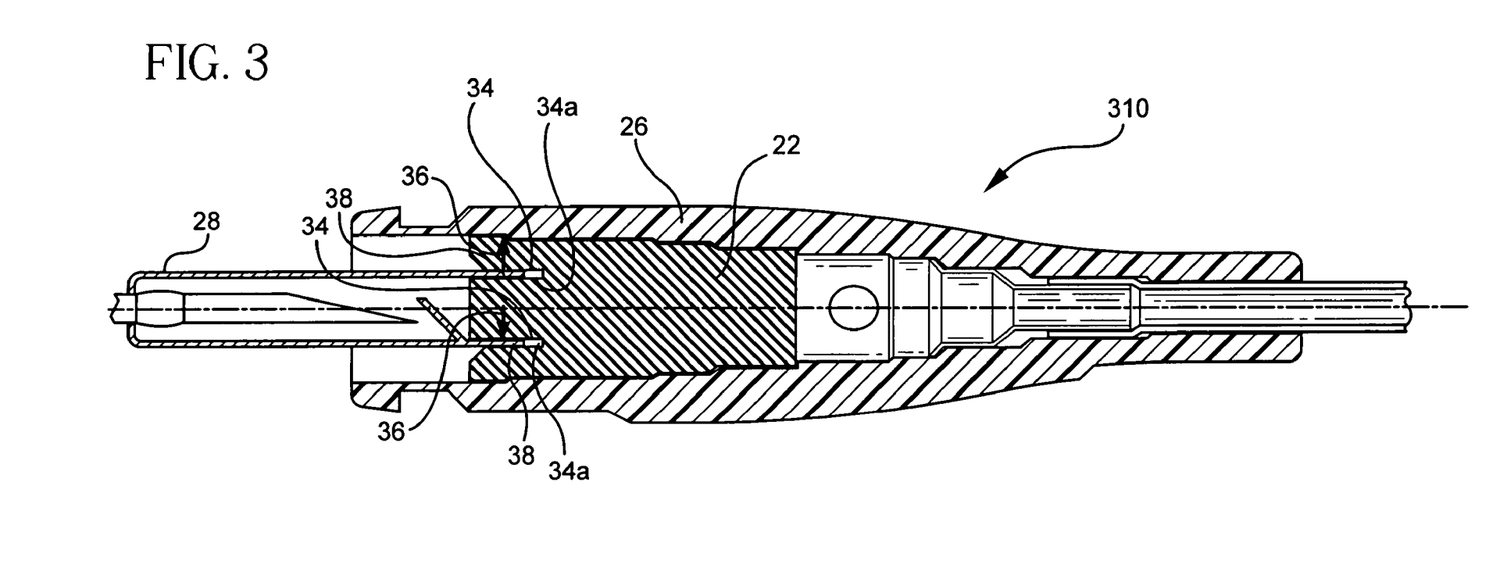
FIG. 3 is a perspective view of another embodiment of a catheter device of the present invention in which the needle has been passed through the septum.

Referring now to FIG. 3, an additional embodiment of a catheter device 310 is illustrated. Again, the catheter device 310 is similar to the embodiments of the catheter devices 10, 210 described above. In fact, the only difference between the catheter device 310 and the devices 10, 210 described above is that in the catheter device 310, no detents or nooks are used to secure/engage the septum 22 to the needle shield 28. Rather, the engagement between the septum 22 and the needle shield 28 occurs exclusively between the receiving portion 34 of the septum 22 and the front edge 38 of the needle shield 28.

The fact that the catheter device 310 lacks detents or nooks may, in some embodiments, be advantageous. For example, the lack of detents or nooks on the catheter device 310 may simplify the manufacturing processes and/or reduce the costs associated with producing the catheter device 310. Accordingly, a manufacturer concerned with cost and production difficulties may choose to manufacture/sell the catheter device 310 rather than the devices 10, 210 disclosed above.

Figure 4A:
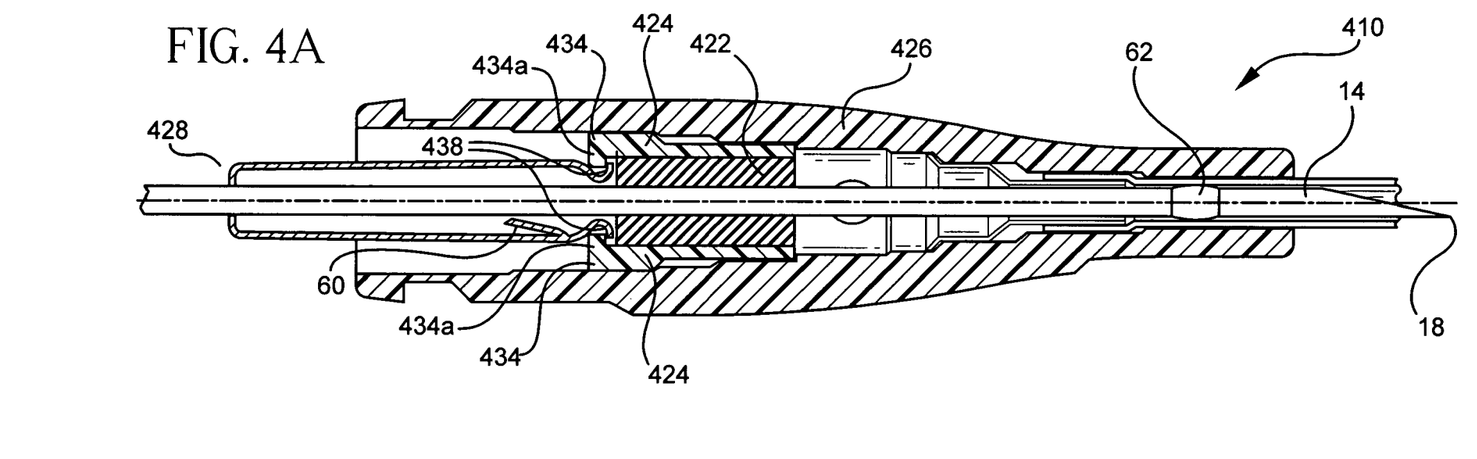
FIG. 4A is a perspective view of a catheter device according to the present invention in which the needle has been passed through the septum.

Referring now to FIG. 4A, an additional catheter device 410 according to the present embodiments is illustrated. Again, the catheter device 410 is similar to the catheter devices 10, 210, 310 disclosed above. As shown in FIG. 4A, the catheter device 410 includes a septum 422 that is contained within a housing 426. However, unlike the previously-described embodiments, the septum 422 includes a septum housing 424 that encircles the other portions of the septum 422. The septum housing 424 is configured such that it will engage the housing 426 and secure the septum 422 in the proper position. The septum housing 424 will also engage the outer housing 426.

As is known in the art, a needle 14 will be passed through the septum 422. The septum 422 will also include a receiving portion 434. However, unlike the previously described embodiments, the receiving portion 434 is not an opening in the septum 422. Rather, in the embodiment shown in FIG. 4A, the receiving portion 434 is a section 434a of the septum housing 424. More particularly, the receiving portion 434 is a section 434a that extends inward towards the septum 422 and is designed to engage/contact with a portion of a needle shield 428—i.e., the front edges 438.

This engagement between the receiving portion 434 and the needle shield 428 will now be explained. Specifically, the needle shield 428 includes a front edge 438 that extend outwardly away from the center of the septum 422. This outward expansion means that the front edges 438 will contact the receiving portion 434. Such contact blocks movement of the needle shield 428 and holds the shield 428 in the proper position.

Figure 4B:
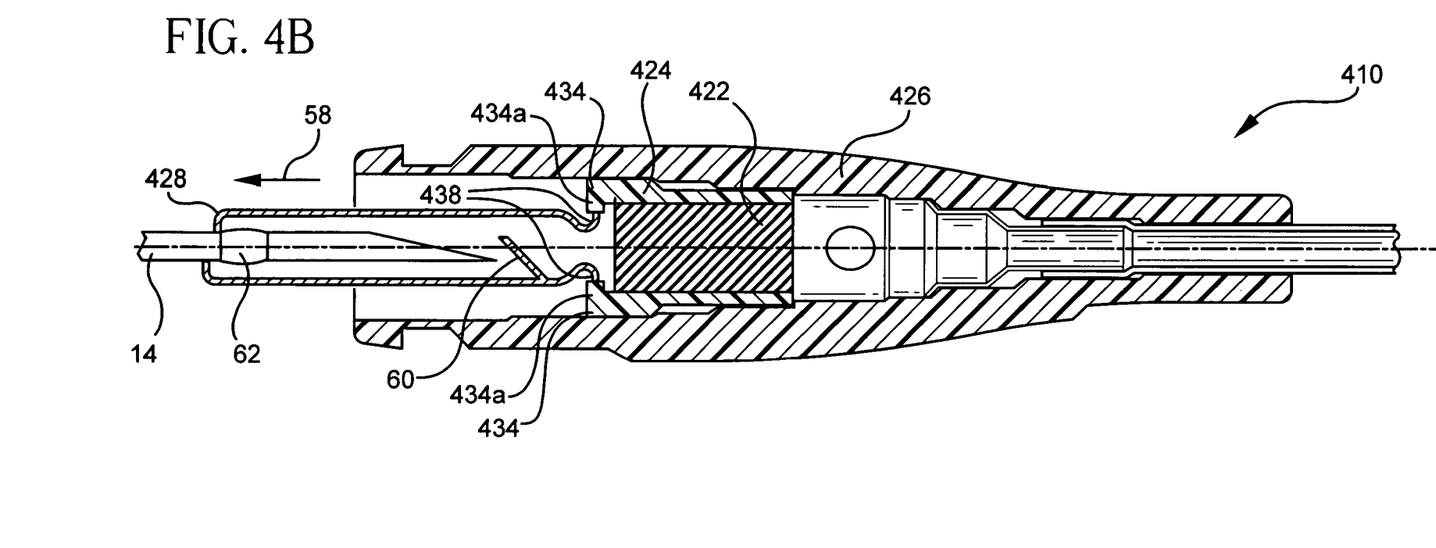
FIG. 4B is a perspective view of a catheter device of FIG. 4A in which the needle has been withdrawn from the septum.

Referring now to FIG. 4B, the catheter device 410 is illustrated after the needle 14 has been withdrawn into the needle shield 428—i.e., withdrawn in the direction indicated by arrow 58. As can be seen from this Figure, once the needle 14 is withdrawn, the needle 14 will no longer push outwardly on the front edges 438. In turn, this removal of the needle 14 will cause the front edges 438 to contract inwardly such that the front edges 438 will slide past the receiving portion 434.

Figure 4C:
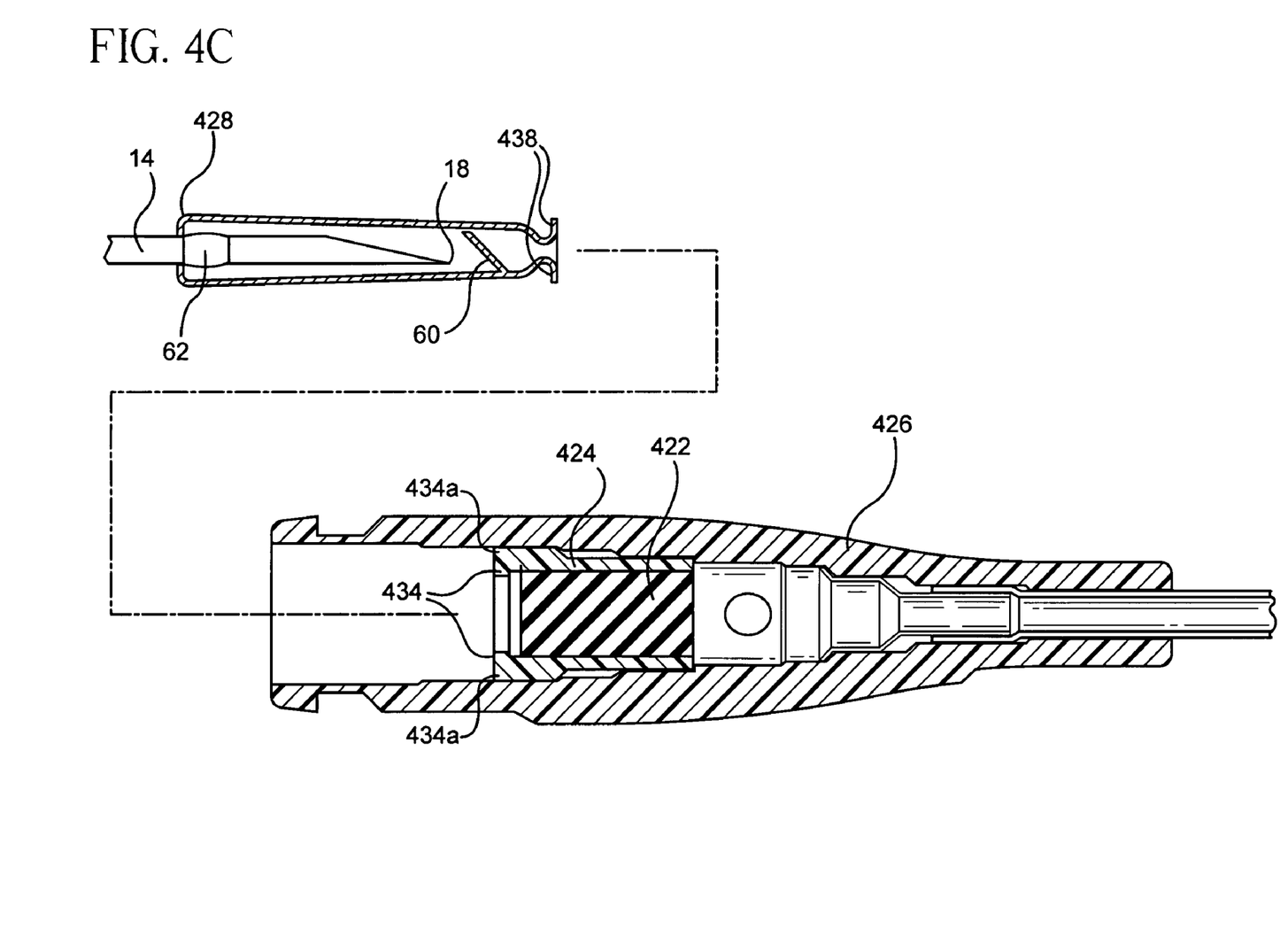
FIG. 4C is a perspective view of a catheter device of FIG. 4A in which the needle shield has been separated from the septum.

Referring now to FIG. 4C, the catheter device 410 is illustrated after front edges 438 have slid past the receiving portion 434. Specifically, once such movement has occurred, there is no longer sufficient force that connects the needle shield 428 to the housing 426. Accordingly, the needle shield 428 is thus removed so that the clinician may properly dispose of the needle 14 and use the catheter device 410.

Figure 5A:
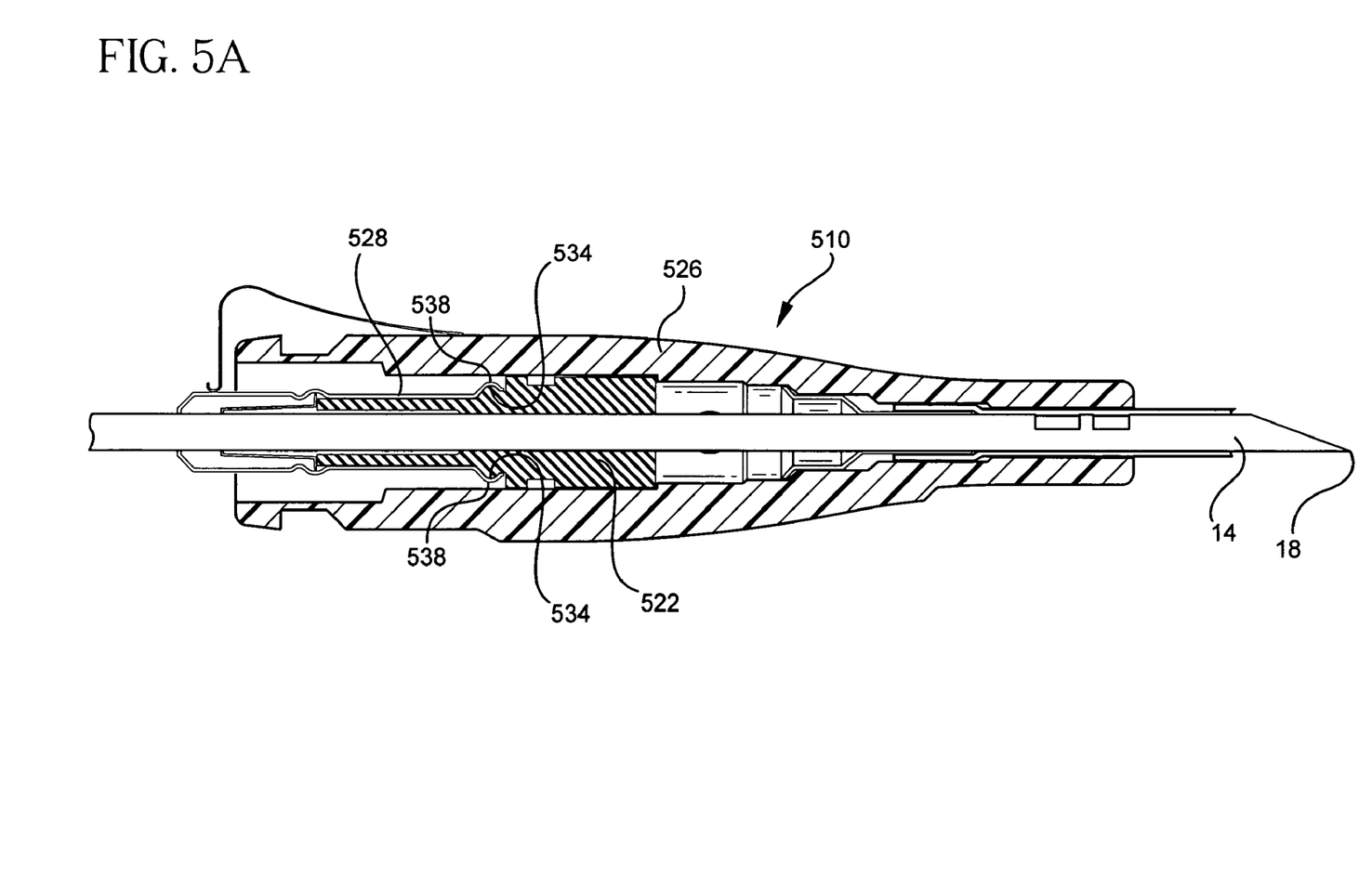
FIG. 5A is a perspective view of a catheter device according to the present invention in which the needle has been passed through the septum.
Figure 5B:
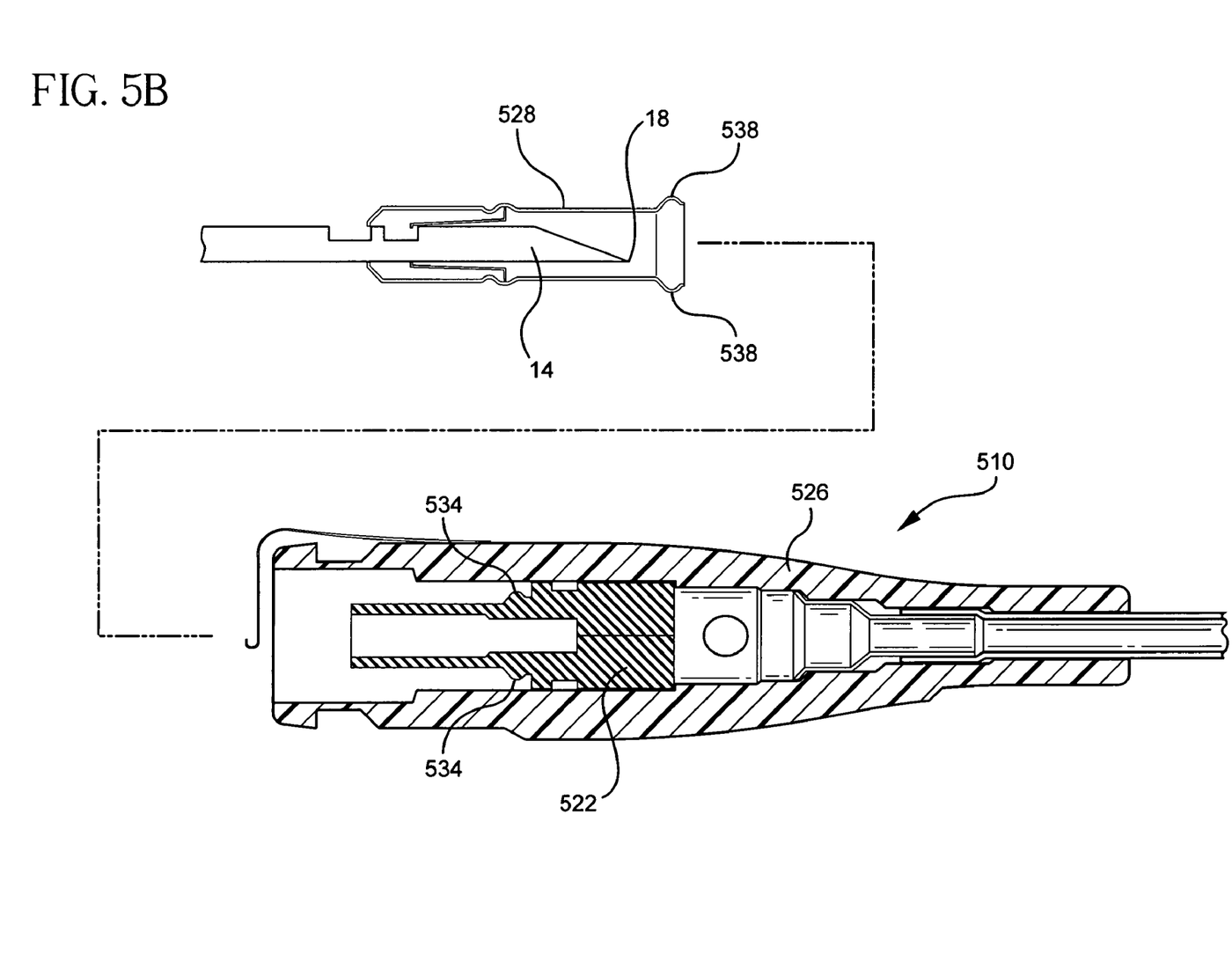
FIG. 5B is a perspective view of a catheter device of FIG. 5A in which the needle shield has been separated from the septum.

Referring now to FIGS. 5A and 5B, an additional embodiment of a catheter device 510 is illustrated. The catheter device 510 is similar to the embodiments disclosed in the patent application entitled "One Piece Low Drag Septum" which was co-invented by the present inventor is owned by the assignee of the present application. This application is incorporated herein by reference.

The catheter device 510 is similar to the embodiments described above. Specifically, the catheter device 510 is designed such that the needle 14 may be passed through the device 510. The catheter device 510 also includes a septum 522 and a needle shield 528.

As with the prior embodiments, the septum 522 is designed to engage with the needle shield 528. Accordingly, the septum 522 includes a receiving portion 534. In the present case, the receiving portion 534 comprises one or more interlock features 534a that are designed to engage the front edges 538 of the needle shield 528 (as shown in FIG. 5B).

However, as shown by FIG. 5B, the catheter device 510 is designed such that when the needle 14 is withdrawn into the needle shield 528—i.e., withdrawn in the direction of the arrow 58—then the detents 534a will disengage from the front edges 538 and the needle shield 528 will be separated from the septum 522.

Figure 6A:
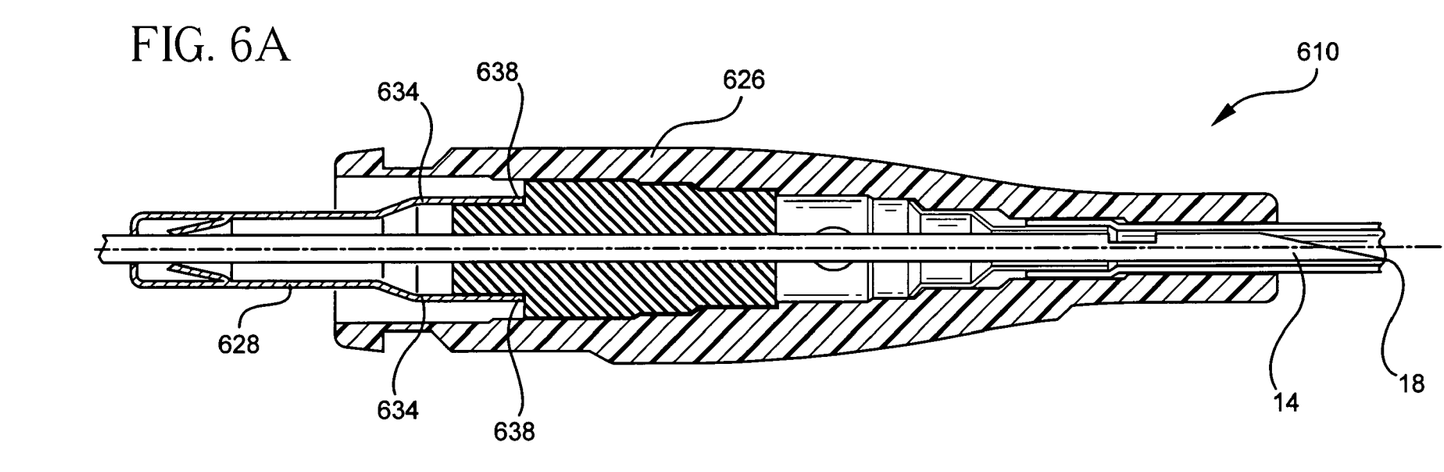
FIG. 6A is a perspective view of a catheter device according to the present invention in which the needle has been passed through the septum.
Figure 6B:
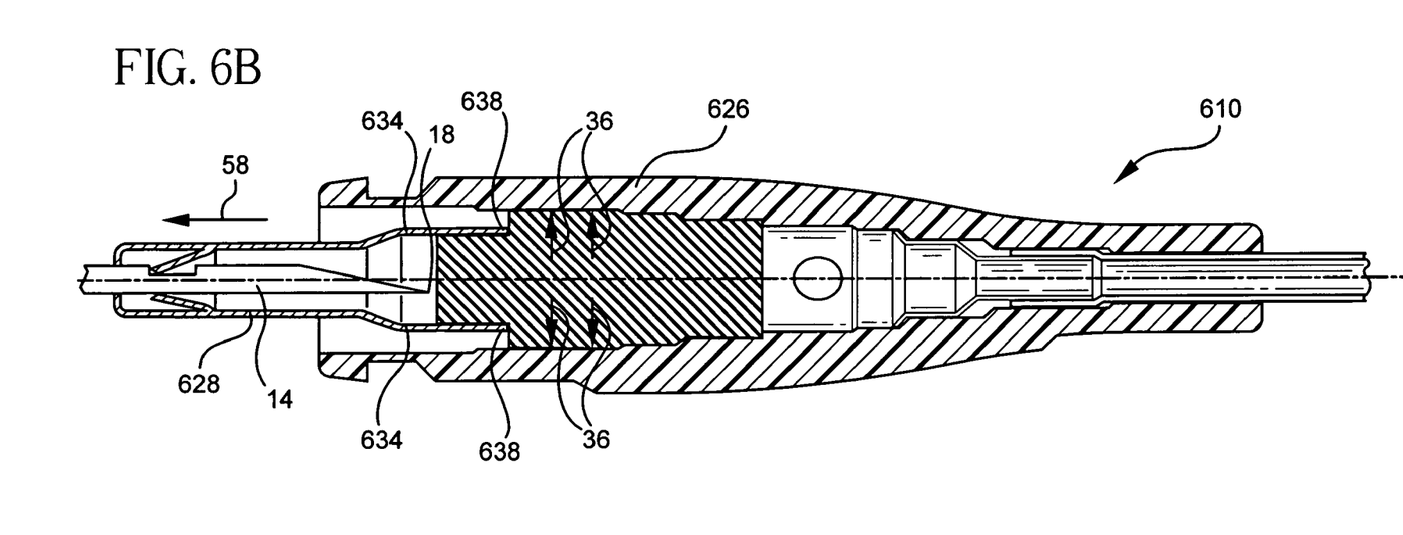
FIG. 6B is a perspective view of a catheter device of FIG. 6A in which the needle has been withdrawn from the septum.

Referring now to FIGS. 6A and 6B, an additional embodiment is illustrated. Specifically, these figures disclose a catheter device 610 that is similar to the catheter devices 10, 210, 310, 410, 510 described above. Thus, the catheter device 610 includes a housing 626 that encloses/houses a septum. The catheter device 610 is also designed such that a needle 14 may be passed through the septum and the catheter device 610.

The catheter device 610 also includes a needle shield 628 that is designed to retain the needle 14 (and, more particularly, the needle tip 18). The catheter device 610 is also designed such that the septum will engage with the needle shield 628. The septum will include a receiving portion 634 that is designed to engage a front edge 638 of the housing 626. In the embodiment shown in FIGS. 6A and 6B, this receiving portion 634 is a flat surface on a proximal portion of the septum. Accordingly, when the needle 14 is passed through the septum 622, the needle 14 will cause the septum to expand such that the receiving portion 634 will engage/contact the front edges 638 of the needle shield 628 (as illustrated in FIG. 6A).

However, as shown in FIG. 6B, when the needle 14 is withdrawn into the needle shield 628 (in the direction of arrow 58), the needle 14 will no longer contact the septum. This lack of contact means that the needle 14 cannot expand the septum, and thus, the septum will contract. In turn, this contraction of the septum means that the receiving portion 634 will no longer contact the needle shield 628/front edge 638. As a result, the needle shield 628 may be withdrawn from the catheter device 610 so that the needle may be disposed of properly.

Referring now to FIGS. 7A through 7D, an additional embodiment is depicted. Specifically, these figures disclose a catheter device that is similar to the catheter devices 10, 210, 310, 410, 510, 610 described above. Thus, the catheter device includes a housing 726 that encloses/houses a septum 722.

Figure 7A:
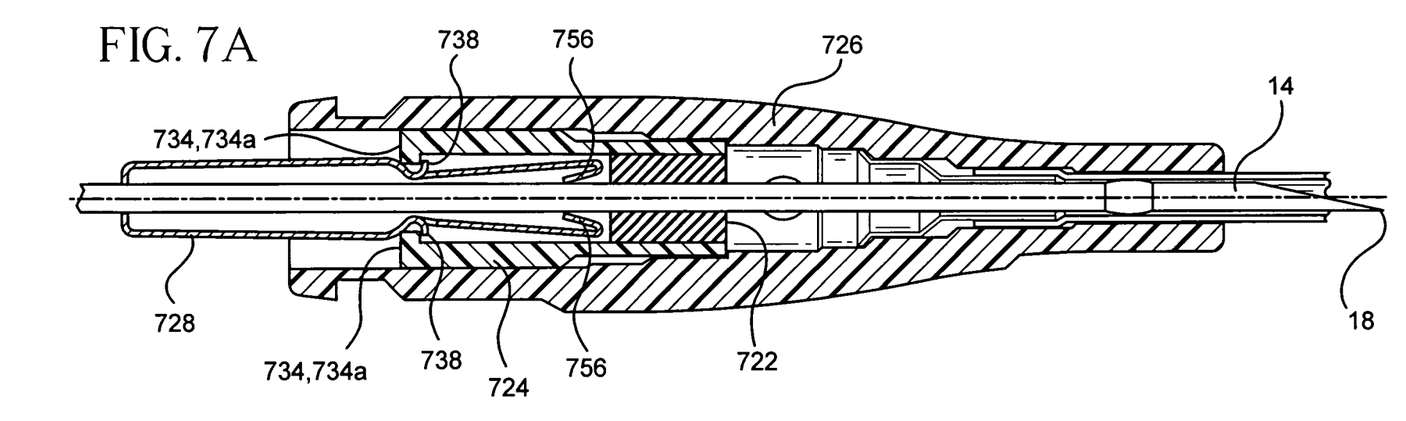
FIG. 7A is a perspective view of a catheter device according to the present invention in which the needle has been passed through the septum.

As with the embodiment shown in FIG. 4A, the septum 722 includes a septum housing 724 that encircles the other portions of the septum 722. The septum housing 724 is configured such that it will engage the housing 726 and secure the septum 722 in the proper position. The septum housing 724 will also engage the outer housing 726.

As is known in the art, a needle 14 will be passed through the septum 722. The septum 722 will also include a receiving portion 734. However, unlike the previously described embodiments, the receiving portion 734 is not an opening in the septum 722. Rather, as with the embodiment discussed above in conjunction with FIG. 4A, the receiving portion 734 is a section 734a of the septum housing 724. More particularly, the receiving portion 734 is a section 734a that extends inward towards the septum 722 and is designed to engage/contact with a portion of a needle shield 728—i.e., the front edges 738.

This engagement between the receiving portion 734 and the needle shield 728 will now be explained. Specifically, the needle shield 728 includes a front edge 738 that extend outwardly away from the center of the septum 722. This outward expansion means that the front edges 738 will contact the receiving portion 734. Such contact blocks movement of the needle shield 728 and holds the shield 728 in the proper position.

It should also be noted that the needle shield 728 that is shown in FIG. 7A differs from that which has been shown in the previous embodiments. Unlike the embodiments shown above, the needle shield 728 is designed such that the barrier 756—i.e., the prong or feature that operates to lock the needle tip 18 within the needle shield 728—is located distal of the interconnection between the front edges 738 and the receiving portion 734. Those of skill in the art will recognize that a variety of other types of needle shields and needle shielding devices may be used as the needle shield 728.

Figure 7B:
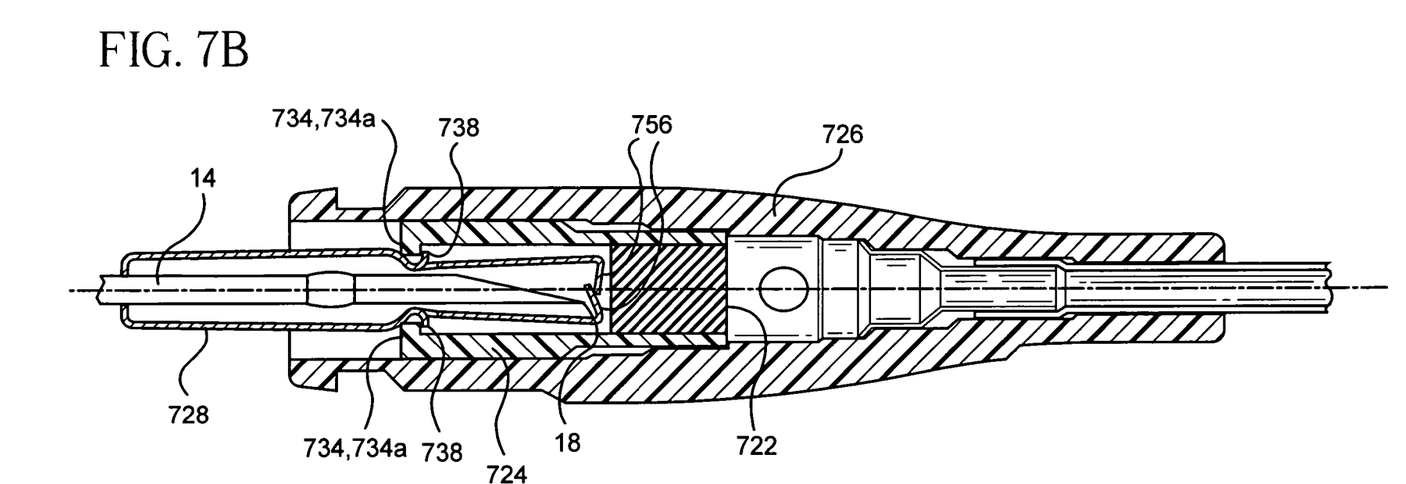
FIG. 7B is a perspective view of a catheter device of FIG. 7A in which the needle has been withdrawn from the septum.

Referring now to FIG. 7B, the catheter device 410 is illustrated after the needle 14 has been withdrawn into the needle shield 728—i.e., after the needle tip 18 has been placed behind the barrier 756. However, as shown in FIG. 7B, the needle 14 is still in a position to push outwardly against the front edges 738. Accordingly, this outward force pushing against the edges 738 causes the edges to engage the receiving portion 734, thereby preventing the needle shield 728 from separating from the septum housing 724.

Figure 7C:
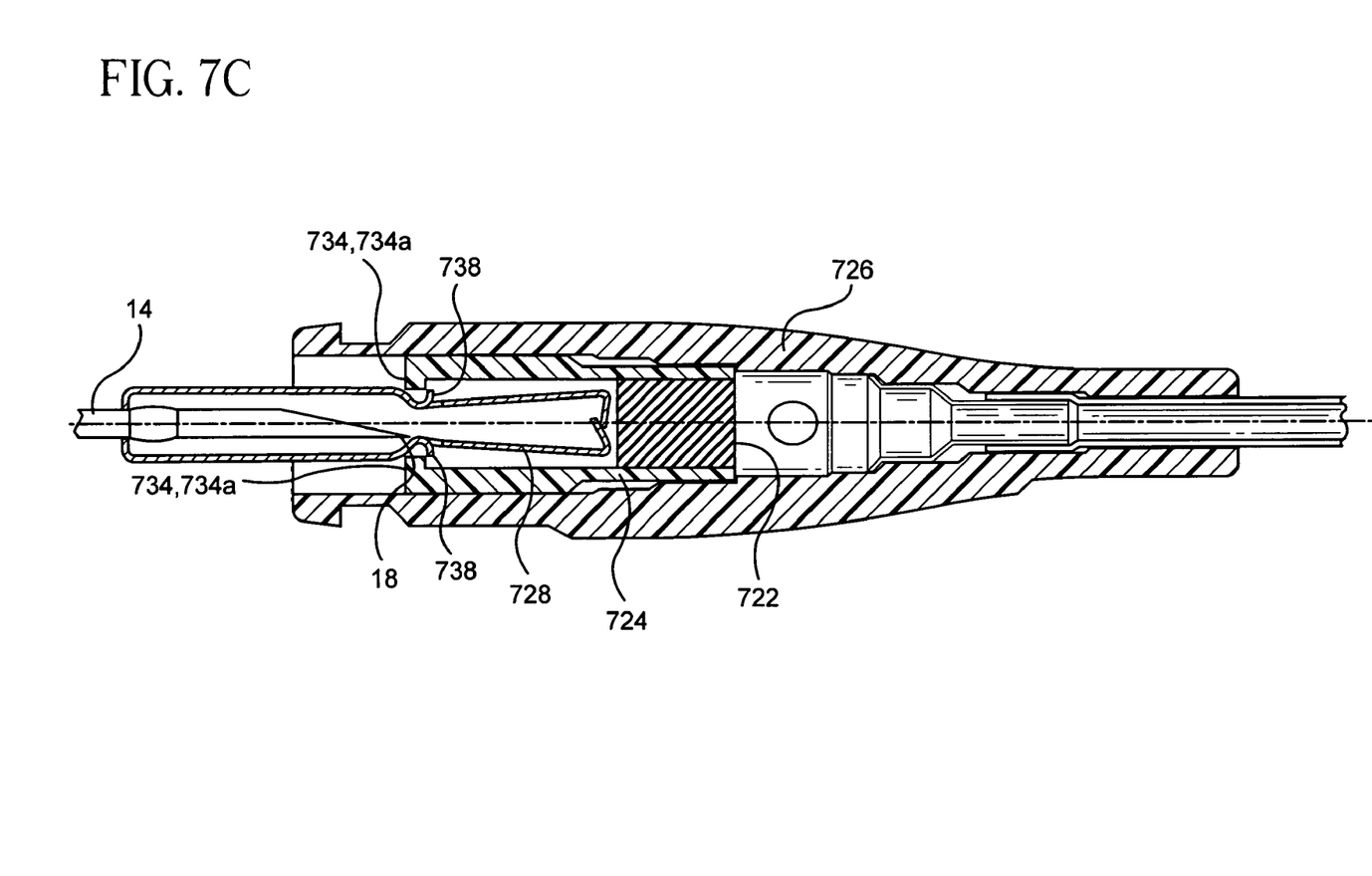
FIG. 7C is a perspective view of the catheter device of FIG. 7A in which the needle has been withdrawn sufficiently such that the needle shield may disengage from the septum housing.

Referring now to FIG. 7C, the catheter device is illustrated after the needle 14 has been withdrawn past the front edges 738. Accordingly, because the needle 14 no longer pushes outwardly on the front edges 738, the front edges 738 may contract such that the needle shield 728 and the front edges 738 will slide past the receiving portion 734 (in the manner described above).

Figure 7D:
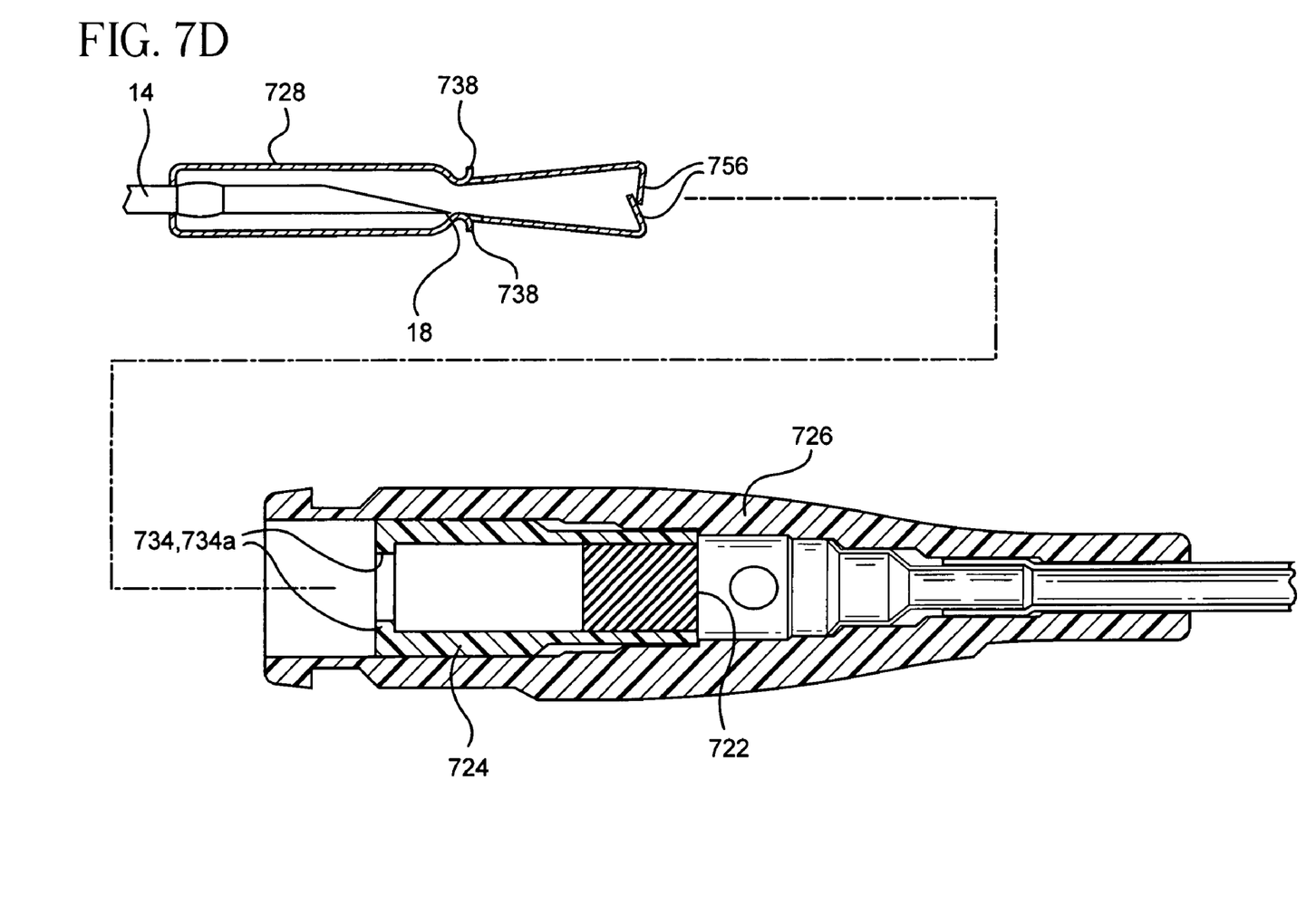
FIG. 7D is a perspective view of a catheter device of FIG. 7A in which the needle shield has been separated from the septum.

Referring now to FIG. 7D, the catheter device is illustrated after front edges 738 have slid past the receiving portion 734. Specifically, once such movement has occurred, there is no longer sufficient force that connects the needle shield 728 to the housing 726. Accordingly, the needle shield 728 is thus removed so that the clinician may properly dispose of the needle 14 and use the catheter device.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. A catheter device comprising:
   a housing having a proximal end and a distal end;
   a needle disposed within the housing, the tip of the needle extending through the distal end of the housing
   a septum disposed within the housing and having a receiving portion;
   a needle shield disposed within the housing and proximal from the septum, the needle shield engaging the receiving portion of the septum when the needle is disposed within the housing;
   wherein the receiving portion of the septum is an interlock feature comprising one or more nooks that directly engage a detent on the needle shield; and
   wherein when the needle is withdrawn proximally through the housing, the needle shield disengages from the receiving portion of the septum and shields the tip of the needle.

2. The device of claim 1, wherein the septum further comprises a nose.

3. The device of claim 1 wherein the septum comprises a septum housing, wherein the receiving portion is a portion of the septum housing.

4. The device of claim 1 wherein the receiving portion is an opening in the septum.

5. The device of claim 1 wherein the septum is an expanding elastomeric seal.

6. The device of claim 1 wherein the receiving portion is a flat surface.

7. The device of claim 1 wherein front edges of the needle shield engage the septum.

8. The device of claim 1 wherein the needle shield comprises a barrier which locks the needle tip in the shield.

9. A catheter device comprising:
   a housing
   a septum disposed within the housing, the septum having a receiving means wherein the receiving means comprises a receiving portion; and
   a needle shield having a means for engaging the receiving means, wherein the needle shield is configured to retain a needle when the needle is withdrawn from the housing, and wherein the needle shield is configured such that when the needle is withdrawn, the engagement means disengages from the receiving means; and
   wherein the receiving portion includes an interlock feature comprising one or more nooks that directly engage a detent on the needle shield.

10. The device of claim 9 wherein the septum comprises a septum housing, wherein the receiving portion is a portion of the septum housing.

11. The device of claim 9 wherein the receiving portion is an opening in the septum.

12. A catheter device comprising:
    a housing having a proximal end and a distal end;
    a needle disposed within the housing, the tip of the needle extending through the distal end of the housing
    an elastomeric septum disposed within the housing and having a receiving portion, the receiving portion having a nook;
    a needle shield disposed within the housing and proximal from the septum, the needle shield directly engaging the nook of the receiving portion of the septum via a detent when the needle is disposed within the housing;
    wherein when the needle is withdrawn proximally through the housing, the needle shield disengages from the nook of the receiving portion of septum and shields the tip of the needle.

13. The device of claim 12 wherein the needle shield comprises a detent which is positionable within the nook prior to disengagement of the septum and the needle shield.

14. The device of claim 12 wherein when the needle is disposed within the septum, the detent is held within the nook.

* * * * *